United States Patent
Lin et al.

(10) Patent No.: US 11,497,728 B2
(45) Date of Patent: Nov. 15, 2022

(54) PREPARATION METHOD FOR LIPOSOME HAVING ABILITY TO STABLY ENCAPSULATE ACTIVE INGREDIENT

(71) Applicant: TCI CO., LTD., Taipei (TW)

(72) Inventors: Yung-Hsiang Lin, Taipei (TW); Hui-Hsuan Liu, Taipei (TW)

(73) Assignee: TCI CO., LTD., Taipei (TW)

( * ) Notice: Subject to any disclaimer, the term of this patent is extended or adjusted under 35 U.S.C. 154(b) by 103 days.

(21) Appl. No.: 17/133,669

(22) Filed: Dec. 24, 2020

(65) Prior Publication Data

US 2022/0125758 A1  Apr. 28, 2022

(30) Foreign Application Priority Data

Oct. 23, 2020 (TW) ................. 109136998

(51) Int. Cl.
*A61K 31/375* (2006.01)
*A61K 9/127* (2006.01)

(52) U.S. Cl.
CPC .......... *A61K 31/375* (2013.01); *A61K 9/1277* (2013.01)

(58) Field of Classification Search
None
See application file for complete search history.

(56) References Cited

U.S. PATENT DOCUMENTS

2007/0082042 A1  4/2007  Park et al.

FOREIGN PATENT DOCUMENTS

CN  102805730 A  12/2012

OTHER PUBLICATIONS

Qiaobin Hu, Hannah Gerhard, Indu Upadhyaya, Kumar Venkitanarayanan, and Yangchao Luo. "Antimicrobial eugenol nanoemulsion prepared by gum arabic andlecithin and evaluation of drying technologies." International Journal of Biological Macromolecules, vol. 87 (2016), pp. 130-140. (Year: 2016).*
Balamurugan K and Chintamani P. "Lipid nano particulate drug delivery: An overview of the emerging trend." The Pharma Innovation Journal, vol. 7(7), 2018, pp. 779-789. (Year: 2018).*
C.K. Pua, N. Sheikh Abd. Hamid, G. Rusul, R. Abd. Rahman. "Production of drum-dried jackfruit (Artocarpus heterophyllus) powder with different concentration of soy lecithin and gum arabic." Journal of Food Engineering, vol. 78, 2007, pp. 630-636. (Year: 2007).*
Enrique Flores-Andrade et al. "Carotenoid nanoemulsions stabilized by natural emulsifiers: Whey protein, gum Arabic, and soy lecithin." Journal of Food Engineering, vol. 290, 2021, Article 110208, pp. 1-8. (Year: 2021).*

* cited by examiner

*Primary Examiner* — Isaac Shomer
(74) *Attorney, Agent, or Firm* — Chieh-Mei Wang

(57) ABSTRACT

A preparation method for a liposome having the ability to stably encapsulate an active ingredient is provided. The preparation method includes providing a mixture and homogenizing the mixture at 300 bar-400 bar to form a liposome suspension. The mixture includes 0.1 wt % of lecithin, 2 wt %-5 wt % of Arabic gum and 63.9125 wt %-97.9 wt % of a solvent. The liposome suspension includes a plurality of liposomes.

7 Claims, 10 Drawing Sheets

US 11,497,728 B2

PREPARATION METHOD FOR LIPOSOME HAVING ABILITY TO STABLY ENCAPSULATE ACTIVE INGREDIENT

CROSS-REFERENCE TO RELATED APPLICATION

This non-provisional application claims priority under 35 U.S.C. § 119(a) to Patent Application No. 109136998 filed in Taiwan, R.O.C. on Oct. 23, 2020, the entire contents of which are hereby incorporated by reference.

BACKGROUND

Technical Field

The instant disclosure relates to a preparation method for a liposome, in particular to a preparation method for a liposome having the ability to stably encapsulate an active ingredient.

Related Art

Due to changes in food culture, the number of people eating outside of home or eating processed food is gradually increased. In order to meet basic nutritional needs of the human body by ingestion, different from obtaining required nutrients only through natural food in the past, nutritional supplements gradually appear in people's lives.

There are many types of nutritional supplements, and there are also many choices in forms, dosage forms and ingestion methods of nutritional supplements. For example, nutritional supplements can be water-soluble vitamins, fat-soluble vitamins, minerals, collagen and the like. In addition, common nutritional supplement forms can be powders, capsules, tablets (such as oral tablets and chewing tablets), liquids (such as effervescent tablets and granules) and the like, and the absorption rate and absorption speed of nutritional supplements in the digestive tract of the human body can be affected by different forms or dosage forms. Theoretically, the absorption rate and absorption speed of nutritional supplements in the forms of liquids, powders, capsules and tablets are gradually reduced. In addition, quick-acting dosage forms and sustained-release dosage forms of nutritional supplements are also developed for absorption in recent years.

Vitamin C (also known as vitamin C) is taken as an example. Vitamin C can be ingested from vegetables and fruits and can also be ingested from nutritional supplements. In addition, common vitamin C dosage forms include oral tablets, chewing tablets, bubble tablets, granules and powders.

SUMMARY

In some embodiments, a preparation method for a liposome having the ability to stably encapsulate an active ingredient includes providing a mixture and homogenizing the mixture at 300 bar-400 bar to form a liposome suspension. The mixture includes 0.1 wt % of lecithin, 2 wt %-5 wt % of Arabic gum and 63.9125 wt %-97.9 wt % of a solvent. The liposome suspension includes a plurality of liposomes.

In some embodiments, the solvent is water.

In some embodiments, the mixture further includes 5 wt %-30 wt % of an active ingredient.

In some embodiments, a content of the active ingredient is 10 wt %.

In some embodiments, the active ingredient is vitamin C.

In some embodiments, the step of providing a mixture includes stirring 0.1 wt % of lecithin, 2 wt %-5 wt % of Arabic gum and 63.9125 wt %-97.9 wt % of the solvent to form a solution and filtering the solution through an 80-mesh sieve to form a mixture.

In some embodiments, the temperature of the mixture in the step of homogenizing the mixture is 40° C.-60° C., the step of homogenizing the mixture to form a liposome suspension includes sterilizing the mixture at 95° C. for 30 minutes and homogenizing the sterilized mixture at 300 bar-400 bar to form a liposome suspension, and the liposome suspension includes a plurality of liposomes.

In some embodiments, the homogenization temperature in the step of homogenizing the mixture is room temperature, and the step of homogenizing the mixture to form a liposome suspension includes homogenizing the mixture at 300 bar-400 bar to form a liposome suspension including a plurality of liposomes and sterilizing the liposome suspension at 95° C. for 30 minutes.

In some embodiments, each liposome is of a hollow spheric structure.

In conclusion, a preparation method for a liposome having the ability to stably encapsulate an active ingredient according to any example includes mixing lecithin, Arabic gum and water at a specific ratio and homogenizing the mixture at a specific pressure to form a liposome suspension. The liposome suspension includes a plurality of liposomes with stable structures. In addition, a preparation method for a liposome having the ability to stably encapsulate an active ingredient according to any example can be used to prepare a liposome in which an active ingredient is encapsulated. Herein, the prepared liposome has a stable structure, can stably encapsulate an active ingredient and can be used to increase the bioabsorption rate of the encapsulated active ingredient.

DETAILED DESCRIPTION

Figure 1:
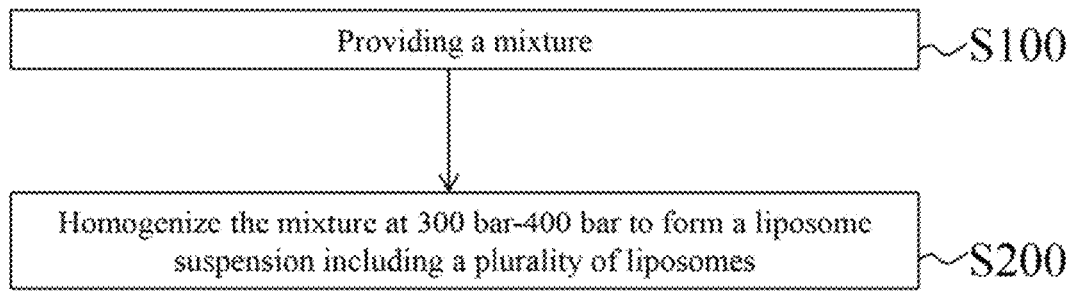
FIG. 1 is a flowchart showing preparation of a liposome having the ability to stably encapsulate an active ingredient in any example.
Figure 5:
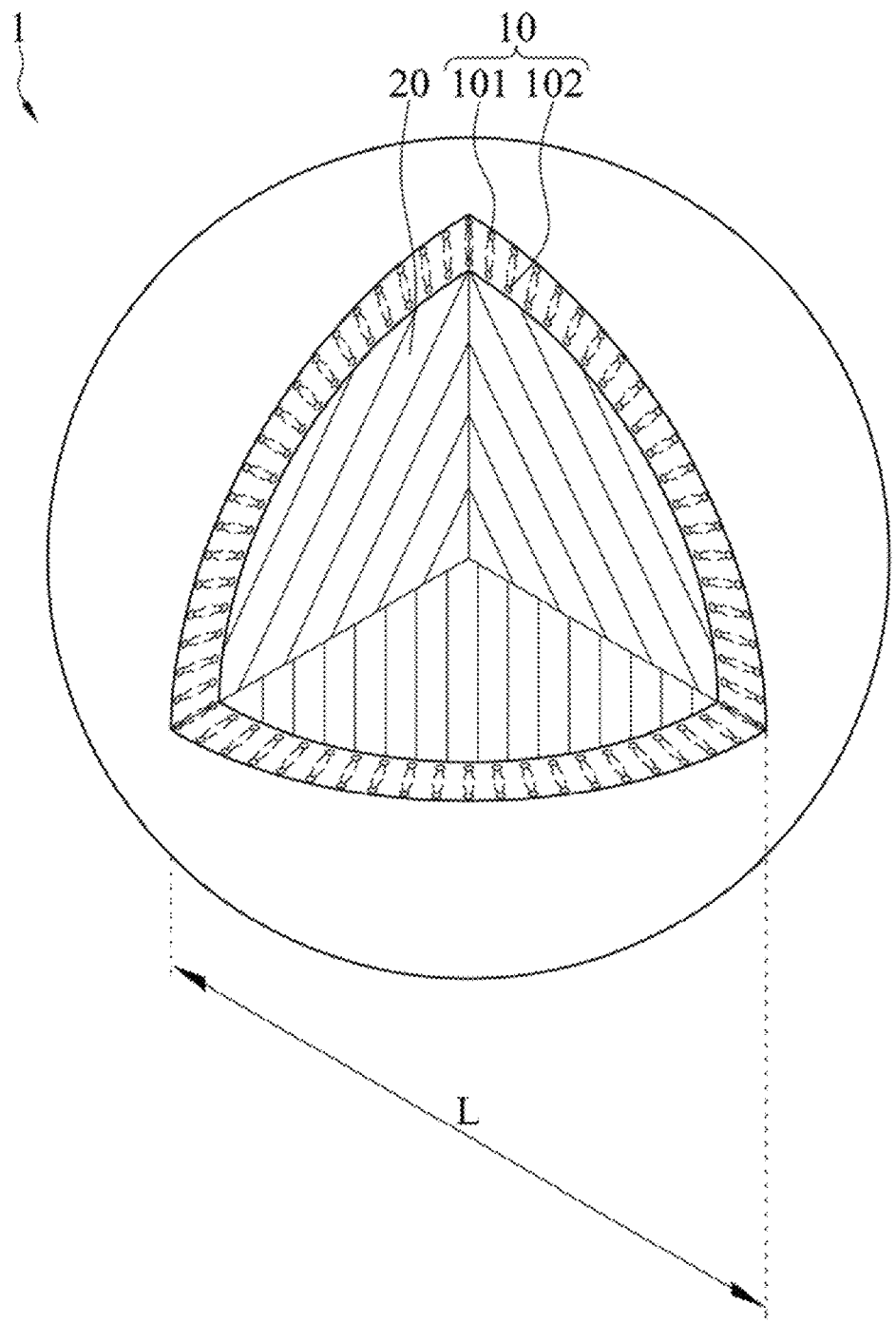
FIG. 5 is a cross-sectional view of a liposome in some embodiments.

In reference to FIG. 1 and FIG. 5, in some embodiments, a mixture is stirred first (step S100) and then homogenized at 300 bar-400 bar to form a liposome suspension including a plurality of liposomes 1 (step S200). The mixture includes 0.1 wt % of lecithin, 2 wt %-5 wt % of Arabic gum and 63.9125 wt %-97.9 wt % of a solvent.

In some embodiments, the lecithin can be, but not limited to, soybean lecithin (SOLEC F). In some embodiments, the solvent can be, but not limited to, water. In some embodiments, the mixture includes 0.1 wt % of soybean lecithin, 2 wt %-5 wt % of Arabic gum and 63.9125 wt %-97.9 wt % of water. For example, a content of the Arabic gum can be 2 wt %, 3 wt %, 4 wt % or 5 wt %.

In some embodiments, the mixture further includes an active ingredient. Thus, the active ingredient can be encapsulated in the formed liposome 1. For example, the active ingredient can be vitamin C, astaxanthin, coenzyme Q10 and the like. In some embodiments, the mixture includes 0.1 wt % of lecithin, 2 wt %-5 wt % of Arabic gum, 5 wt %-30 wt % of the active ingredient and 63.9125 wt %-92.9 wt % of a solvent. For example, a content of the active ingredient is 10 wt %.

In some embodiments, the mixture further includes a thickener. Herein, the thickener is conducive to protecting the structure of the liposome 1. For example, the thickener can be guar gum, Sanxian gum (or named corn sugar gum and xanthan gum) or a combination thereof. In some embodiments, the mixture includes 0.1 wt % of lecithin, 2 wt %-5 wt % of Arabic gum, 5 wt %-30 wt % of an active ingredient, 0.3175 wt %-0.6175 wt % of the thickener and 63.9125 wt %-92.5825 wt % of a solvent. For example, 0.3175 wt %-0.6175 wt % of thickener includes 0.0675 wt % of guar gum and 0.25 wt %-0.55 wt % of Sanxian gum. In some demonstration embodiments, the mixture includes 0.1 wt % of lecithin, 2 wt %-5 wt % of Arabic gum, 10 wt % of the active ingredient, 0.0675 wt % of guar gum, 0.25 wt %-0.55 wt % of Sanxian gum and 83.9125 wt %-87.5825 wt % of water.

In some embodiments, the mixture can further include a food additive. The food additive can be a sweetener, an acidifier, a preservative and the like. The sweetener can be sucralose, the acidifier can be citric acid monohydrate, and the preservative can be potassium sorbate. In some embodiments, the mixture includes 0.1 wt % of lecithin, 2 wt %-5 wt % of Arabic gum, 5 wt %-30 wt % of an active ingredient, 0.3175 wt %-0.6175 wt % of the thickener, 0.07 wt %-0.37 wt % of the food additive and 63.9125 wt %-92.5125 wt % of a solvent. For example, 0.35 wt % of the food additive can be a combination of 0.3 wt % of the acidifier and 0.05 wt % of the preservative, or 0.07 wt % of the food additive can be a combination of 0.02 wt % of the sweetener and 0.05 wt % of the preservative. In some demonstration embodiments, the mixture includes 0.1 wt % of lecithin, 2 wt %-5 wt % of Arabic gum, 10 wt % of the active ingredient, 0.0675 wt % of guar gum, 0.25 wt % of Sanxian gum, 0.05 wt % of the preservative, 0.02 wt % of the sweetener and 84.5125 wt %-87.5125 wt % of water. In other demonstration embodiments, the mixture includes 0.1 wt % of lecithin, 2 wt %-5 wt % of Arabic gum, 10 wt % of the active ingredient, 0.0675 wt % of guar gum, 0.55 wt % of Sanxian gum, 0.05 wt % of the preservative, 0.3 wt % of the acidifier and 83.9325 wt %-86.9325 wt % of water.

Figure 2:
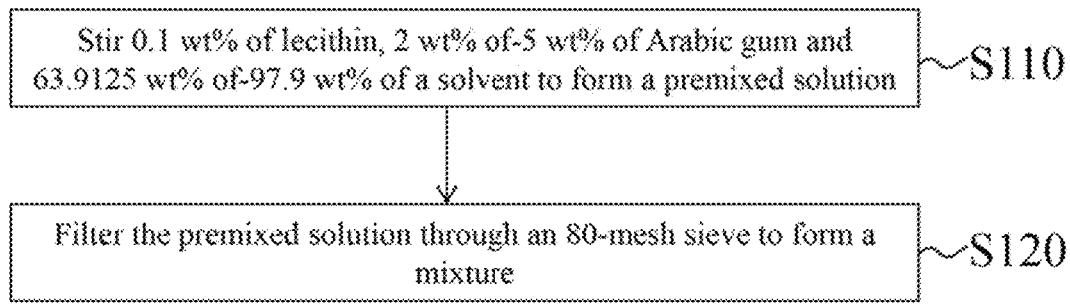
FIG. 2 is a flowchart of step S100.

In reference to FIG. 2, in some embodiments, the step S100 includes the following steps: Stirring 0.1 wt % of lecithin, 2 wt %-5 wt % of Arabic gum and 63.9125 wt %-97.9 wt % of a solvent to form a premixed solution (step S110) and filtering the premixed solution through an 80-mesh sieve to form a mixture (step S120).

Herein, in some embodiments, a powerful stirring device can be used to completely dissolve all components (hereinafter named solutes) except the solvent in the solvent according to actual needs. For example, all solutes can be added into the solvent at once, or different solutes can be added into the solvent sequentially to be dissolved one by one.

In an implementation state of the step S110, 0.1 wt % of lecithin and 2 wt %-5 wt % of Arabic gum are added into 63.9125 wt %-97.9 wt % of a solvent and stirred uniformly to form a premixed solution.

Herein, in other embodiments, when the strength of the stirring device (such as an oscillator) is weak, lecithin, one of the solutes, can be mixed with part of the solvent at a weight ratio (w/w) of 1:50 according to actual needs and stirred at room temperature (25° C.) to dissolve the lecithin in part of the solvent to form a premixed solution (hereinafter named first premixed solution). Besides, the solutes except the lecithin are dissolved in the rest solvent to form a premixed solution (hereinafter named second premixed solution). After it is confirmed that the lecithin is completely dissolved in part of the solvent and the rest solutes are completely dissolved in the rest solvent, the first premixed solution and the second premixed solution are mixed and stirred uniformly to form a premixed solution (hereinafter named third premixed solution). In other words, the solutes (such as the lecithin, the Arabic gum and the like) are separately dissolved in the solvent (such as water) to form a first premixed solution and a second premixed solution, and then the first premixed solution and the second premixed solution are mixed to form a third premixed solution. Thus, full dissolution of the solutes in the solvent is facilitated.

In another implementation state of the step S110, 0.1 wt % of lecithin is dissolved in at least 5 wt % of a solvent to form a first premixed solution, the rest solutes (such as 2 wt %-5 wt % of Arabic gum) are dissolved in the rest solvent (at most 92.9 wt % of the solvent) to form a second premixed solution, and the first premixed solution and the second premixed solution are mixed to form a third premixed solution, or 0.1 wt % of lecithin and 2 wt %-5 wt % of Arabic gum are separately dissolved in 63.9125 wt %-97.9 wt % of the solvent and mixed one by one.

Figure 4:
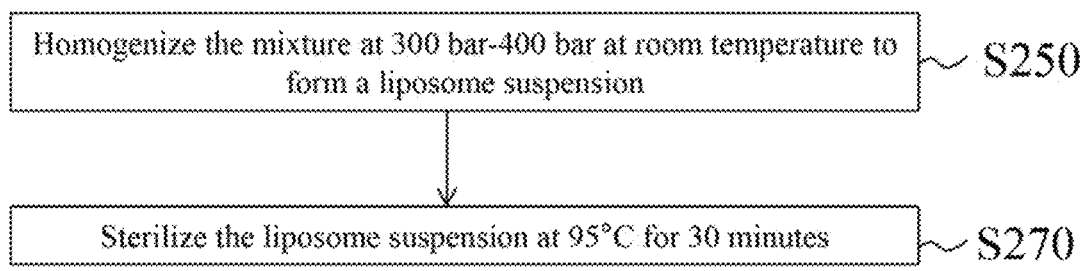
FIG. 4 is a flowchart of step S200 in other embodiments.

In addition, the mixture is homogenized at 300 bar-400 bar to form a liposome suspension after being formed. Herein, a sterilization procedure can be carried out before or after the step of homogenizing the mixture (namely, homogenization treatment), as shown in FIG. 4 and FIG. 5. In some embodiments, the set value of the sterilization procedure is 87° C.±2° C. to 95° C.±5° C. for 30 minutes. For example, on a production line, the set value of the sterilization procedure is 87° C.±2° C. for 30 minutes.

Figure 3:
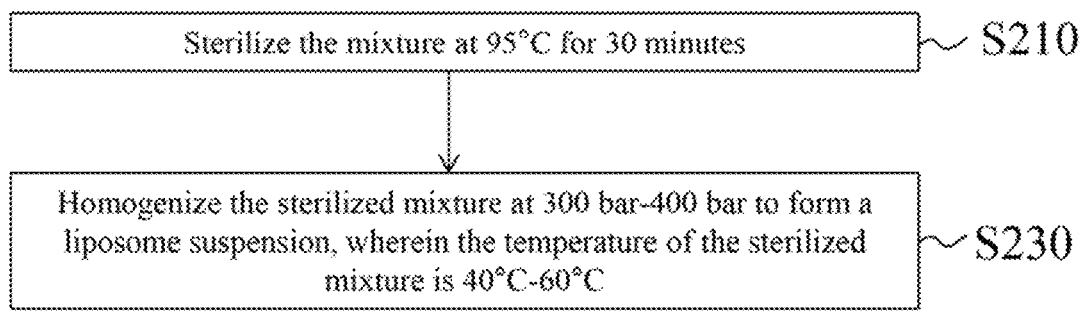
FIG. 3 is a flowchart of step S200 in some embodiments.

In reference to FIG. 3, in some embodiments, the step S200 includes: Sterilizing the mixture at 95° C. for 30 minutes (step S210) and homogenizing the sterilized mixture at 300 bar-400 bar to form a liposome suspension, wherein the temperature of the sterilized mixture is 40° C.-60° C. (step S230). In other words, the process of carrying out a sterilization procedure before the step of homogenizing the mixture is named "pre-sterilization treatment". Herein, the temperature of the mixture to be homogenized in "pre-sterilization treatment" is 40° C.-60° C. For example, the temperature of the mixture to be homogenized in "pre-sterilization treatment" is 50° C.

In some demonstration embodiments, first, the mixture is sterilized with a sterilizing device (namely, step S210), and the sterilized mixture can be homogenized (namely, step S230) when the temperature is reduced to 40° C.-60° C. (such as 50° C.) to form a liposome suspension.

In reference to FIG. 4, in some embodiments, the step 200 includes:

Homogenizing the mixture at 300 bar-400 bar at room temperature to form a liposome suspension (step S250) and sterilizing the liposome suspension at 95° C. for 30 minutes (step S270). In other words, the process of carrying out a sterilization procedure after the step of homogenizing the mixture is named "post-sterilization treatment". Herein, homogenization treatment in "post-sterilization treatment" is carried out at room temperature (25° C.).

In some demonstration embodiments, first, the mixture is homogenized at room temperature (25° C.) to form a liposome suspension (namely, step S250). After the liposome suspension is formed, a sterilization procedure is carried out (namely, step S270).

Herein, homogenization treatment is carried out at a pressure of 300 bar-400 bar, and the mixture containing 0.1 wt % of lecithin, 2 wt %-5 wt % of Arabic gum and 63.9125 wt %-97.9 wt % of a solvent can be fully emulsified to form a liposome suspension. In addition, the liposome suspension contains a plurality of liposomes 1 with stable structures. In addition, since the structure of the prepared liposome 1 is stable, the liposome 1 has the ability to stably encapsulate an active ingredient.

Figure 6:
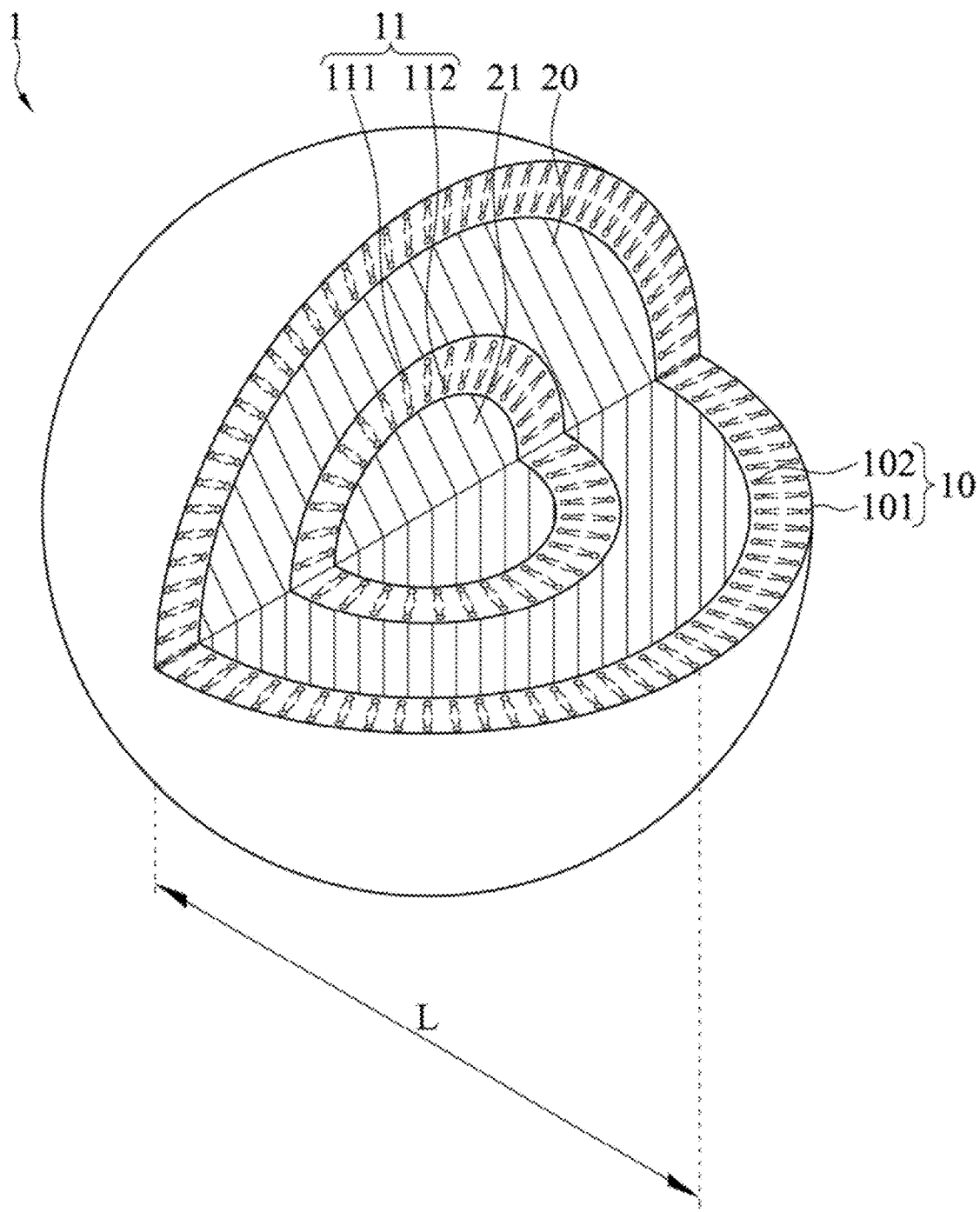
FIG. 6 is a cross-sectional view of a liposome in another example.
Figure 7:
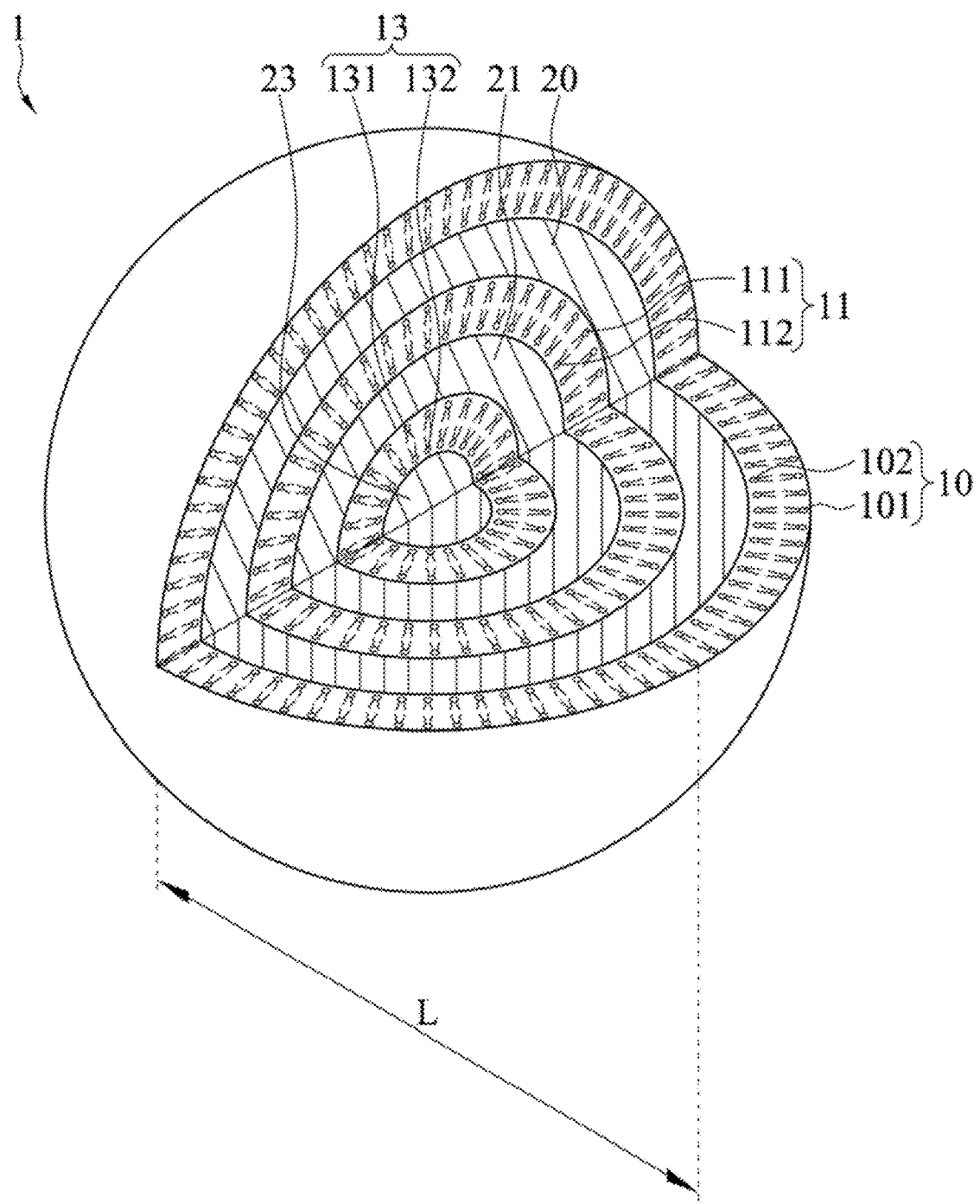
FIG. 7 is a cross-sectional view of a liposome in yet another example.

Moreover, the lecithin can form a liposome 1 with a hollow structure through homogenization treatment at a specific pressure (300 bar-400 bar), as shown in FIG. 5 to FIG. 7.

In reference to FIG. 5 to FIG. 7, in some embodiments, the liposome 1 includes at least one encapsulating layer 10, and each of the encapsulating layer 10 has a hollow spheric structure composed of a bilayered membrane. The bilayered membrane includes a first phospholipid layer 101 and a second phospholipid layer 102. The first phospholipid layer 101 constitutes an outer layer of the hollow spheric structure, the second phospholipid layer 102 constitutes an inner layer of the hollow spheric structure, and the first phospholipid layer 101 and the second phospholipid layer 102 are juxtaposed. The first phospholipid layer 101 and the second phospholipid layer 102 are respectively composed of a plurality of phospholipids, and each phospholipid includes a hydrophilic end and a hydrophobic end. For example, the inner and outer sides of the encapsulating layer 10 are mainly composed of the hydrophilic ends of phospholipids, and the middle section of a bilayered membrane structure is mainly composed of the hydrophobic ends. In other words, the hydrophilic ends of the plurality of phospholipids of the first phospholipid layer 101 face outward and constitute the outer surface of the encapsulating layer 10, and the hydrophilic ends of the plurality of phospholipids of the second phospholipid layer 102 face inward and constitute the inner surface of the encapsulating layer 10. Besides, the hydrophobic ends of the plurality of phospholipids of the first phospholipid layer 101 and the hydrophobic ends of the plurality of phospholipids of the second phospholipid layer 102 are adjacent to each other and are arranged side by side.

In some embodiments, the liposome 1 includes one encapsulating layer 10 and one inner space 20, as shown in FIG. 5. In some demonstration embodiments, the liposome 1 includes an encapsulating layer 10 and an inner space 20. Herein, there is an encapsulating layer 10, and an inner space 20 is formed on the inner side of the encapsulating layer 10.

In some embodiments, the liposome 1 includes a plurality of encapsulating layers 10 and a plurality of inner spaces 20, as shown in FIG. 6 and FIG. 7. In reference to FIG. 6, in some demonstration embodiments, when the liposome 1 includes two encapsulating layers (hereinafter named first encapsulating layer 10 and second encapsulating layer 11) and two inner spaces (hereinafter named first inner space 20 and second inner space 21), the first encapsulating layer 10 as the outermost layer encapsulates the second encapsulating layer 11 with a smaller outer diameter, the first inner space 20 is formed between the first encapsulating layer 10 and the second encapsulating layer 11, and the second inner space 21 is formed on the inner side of the second encapsulating layer 11. The bilayered membrane of the first encapsulating layer 10 includes a first phospholipid layer 101 and a second phospholipid layer 102, and the bilayered membrane of the second encapsulating layer 11 includes a first phospholipid layer 111 and a second phospholipid layer 112.

In reference to FIG. 7, in some demonstration embodiments, when the liposome 1 includes three encapsulating layers (hereinafter named first encapsulating layer 10, second encapsulating layer 11 and third encapsulating layer 13) and three inner spaces (hereinafter named first inner space 20, second inner space 21 and third inner space 23), the first encapsulating layer 10 as the outermost layer encapsulates the second encapsulating layer 11 with a smaller outer diameter, and the first inner space 20 is formed between the first encapsulating layer 10 and the second encapsulating layer 11. Besides, the second encapsulating layer 11 encapsulates the third encapsulating layer 13 with a much smaller outer diameter, the second inner space 21 is formed between the second encapsulating layer 11 and the third encapsulating layer 13, and the third inner space 23 is formed on the inner side of the third encapsulating layer 13. The bilayered membrane of the first encapsulating layer 10 includes a first phospholipid layer 101 and a second phospholipid layer 102, the bilayered membrane of the second encapsulating layer 11 includes a first phospholipid layer 111 and a second phospholipid layer 112, and the bilayered membrane of the third encapsulating layer 13 includes a first phospholipid layer 131 and a second phospholipid layer 132.

It should be particularly noted that the number of the encapsulating layer 10 and the inner space 20 can be, but not limited to, 2, 3 and 4, and these numbers are illustrated as embodiments, but not limited thereto.

In some embodiments, at least one inner space 20 is formed on the inner side of at least one encapsulating layer 10, and can be used for encapsulating an active ingredient. Therefore, when the liposome 1 further includes an active ingredient, the active ingredient can be located in the inner space 20.

In some embodiments, the liposome 1 is of a hollow spheric structure and includes an inner space 20 used for encapsulating an active ingredient. In some embodiments, the liposome 1 includes a plurality of encapsulating layers 10 with hollow spheric structures, and the encapsulating layers 10 incrementally encapsulate in sequence according to the volume size. In addition, since each encapsulating layer 10 is hollow, a plurality of inner spaces 20 are formed among the encapsulating layers 10. Herein, each inner space 20 can be used for encapsulating an active ingredient.

In some embodiments, the outer diameter L of at least one encapsulating layer 10 is 200-400 nm. For example, the outer diameter L of the liposome 1 can be 200 nm, 250 nm, 300 nm, 350 nm and 400 nm.

Herein, in some embodiments, when a mixture containing 5 wt %-30 wt % of active ingredient, 0.1 wt % of lecithin, 2 wt %-5 wt % of Arabic gum and 63.9125 wt %-92.9 wt % of a solvent is homogenized at 300 bar-400 bar to form a liposome suspension containing a plurality of liposomes 1 with stable structures, the obtained liposomes 1 have stable structures and can stably encapsulate an active ingredient,

Example 1: Preparation of a Liposome 1 Containing Vitamin C (Pre-Sterilization Treatment)

Herein, 6 groups of mixtures are prepared according to formula ingredients and formula ratios in Table 1. Control groups include groups C1 to C4, and experimental groups include groups E1 to E1 In addition, a sterilization procedure is carried out before homogenization treatment in groups C1 to C4 and groups E1 to E2. In other words, the preparation process is pre-sterilization treatment in groups C1 to C4 and groups E1 to E2.

TABLE 1

| | Group | | | | | |
| --- | --- | --- | --- | --- | --- | --- |
| | Control group | | | | Experimental group | |
| Formula ingredient | Group C1 | Group C2 | Group C3 | Group C4 | Group E1 | Group E2 |
| Soybean lecithin | 1 | 0.5 | 1 | 0.5 | 0.1 | 0.1 |
| Arabic gum | 5 | 5 | 3 | 3 | 5 | 3 |
| Guar gum (thickener) | 0.0675 | 0.0675 | 0.0675 | 0.0675 | 0.0675 | 0.0675 |
| Sanxian gum (thickener) | 0.25 | 0.25 | 0.25 | 0.25 | 0.25 | 0.25 |
| Sucralose (sweetener) | 0.02 | 0.02 | 0.02 | 0.02 | 0.02 | 0.02 |
| Potassium sorbate (preservative) | 0.05 | 0.05 | 0.05 | 0.05 | 0.05 | 0.05 |
| Water | 83.6125 | 84.1125 | 85.6125 | 86.1125 | 84.5125 | 86.5125 |
| Vitamin C | 10 | 10 | 10 | 10 | 10 | 10 |

Unit: wt %.

and thus the active ingredient in the liposomes can be prevented from being affected by external factors (such as digestive juice).

Moreover, in some embodiments, the liposome suspension containing a plurality of liposomes 1 stably encapsulating an active ingredient can be used as food (such as nutritional supplements), pharmaceuticals or materials used for preparing food or pharmaceuticals.

Herein, when a recipient takes a nutritional supplement prepared from a liposome suspension of the liposome 1 encapsulating an active ingredient (such as vitamin C, astaxanthin and coenzyme Q10), the stable encapsulating structure of the liposome 1 can effectively reduce the effect of the digestive environment of the recipient on the active ingredient (such as destruction or degradation), and the bilayered phospholipid structure of the liposome 1 can make the liposome 1 combined with a cell membrane of the recipient and the active ingredient in the liposome 1 effectively absorbed by the intestines of the recipient.

In some demonstration embodiments, 0.1 wt % of lecithin, 2 wt %-5 wt % of Arabic gum, 10 wt % of vitamin. C and 84.9 wt %-87.9 wt % of water are mixed and stirred uniformly to form a premixed solution. Then, the premixed solution is filtered through an 80-mesh sieve to form a mixture.

In an implementation state, the mixture is sterilized at 95° C.±5° C. for 30 minutes and then homogenized at 300 bar-400 bar to form a liposome suspension, and the liposome suspension contains a plurality of liposomes 1 in which vitamin C is encapsulated.

In another implementation state, the mixture is homogenized at 300 bar-400 bar to form a liposome suspension. Then, the liposome suspension is sterilized at 95° C.±5° C. for 30 minutes. Herein, the liposome suspension contains a plurality of liposomes 1 in which vitamin C is stably encapsulated.

Herein, the total weight of each mixture is 100 grams. First, soybean lecithin and part of water are mixed at a weight ratio (w/w) of 1:50 and stirred at room temperature (25° C.) to confirm that lecithin is dissolved in part of water to form a first premixed solution. Besides, Arabic gum, guar gum, Sanxian gum, sucralose, potassium sorbate, vitamin C and the rest water are mixed to form a second premixed solution. The first premixed solution and the second premixed solution are mixed and stirred uniformly to ensure that soybean lecithin, Arabic gum, guar gum, Sanxian gum, sucralose, potassium sorbate and vitamin C are completely dissolved in water, and water is used for quantification to make the total weight reach 100 grams to form a third premixed solution. Then, the quantified third premixed solution is filtered through an 80-mesh sieve to form a mixture. Herein, the mixtures of all groups contain 10 wt % of vitamin C respectively.

Then, the mixtures are subjected to a sterilization procedure, and the set value of the sterilization procedure is 95° C.±5° C. for 30 minutes. Each sterilized mixture is homogenized with a homogenizer (brand: GEA Niro Soavi, model: Panda Plus) when cooled to 50° C. to form a liposome suspension, wherein the pressure value set in homogenization treatment is 350 bar. Herein, each liposome suspension contains a plurality of liposomes 1 in which vitamin C is encapsulated.

Example 2: Preparation of a Liposome 1 Containing Vitamin C (Post-Sterilization Treatment)

Herein, 6 groups of mixtures are prepared according to formula ingredients and formula ratios in Table 2. Control groups include groups C5 to C8, and experimental groups include groups E3 to E4. In addition, a sterilization procedure is carried out after homogenization treatment in groups C5 to C8 and groups E3 to E4. In other words, the preparation process is post-sterilization treatment in groups C5 to C8 and groups E3 to E4.

TABLE 2

| Formula ingredient | Control group | | | | Experimental group | |
|---|---|---|---|---|---|---|
| | Group C5 | Group C6 | Group C7 | Group C8 | Group E3 | Group E4 |
| Soybean lecithin | 1 | 0.5 | 1 | 0.5 | 0.1 | 0.1 |
| Arabic gum | 5 | 5 | 3 | 3 | 5 | 3 |
| Guar gum (thickener) | 0.0675 | 0.0675 | 0.0675 | 0.0675 | 0.0675 | 0.0675 |
| Sanxian gum (thickener) | 0.25 | 0.25 | 0.25 | 0.25 | 0.25 | 0.25 |
| Sucralose (sweetener) | 0.02 | 0.02 | 0.02 | 0.02 | 0.02 | 0.02 |
| Potassium sorbate (preservative) | 0.05 | 0.05 | 0.05 | 0.05 | 0.05 | 0.05 |
| Water | 83.6125 | 84.1125 | 85.6125 | 86.1125 | 84.5125 | 86.5125 |
| Vitamin C | 10 | 10 | 10 | 10 | 10 | 10 |

Unit: wt %.

Herein, the total weight of each mixture is 100 grams. First, soybean lecithin and part of water are mixed at a weight ratio (w/w) of 1:50 and stirred at room temperature (25° C.) to confirm that lecithin is dissolved in part of water to form a first premixed solution. Besides, Arabic gum, guar gum, Sanxian gum, sucralose, potassium sorbate, vitamin C and the rest water are mixed to form a second premixed solution. The first premixed solution and the second premixed solution are mixed and stirred uniformly to ensure that soybean lecithin, Arabic gum, guar gum, Sanxian gum, sucralose, potassium sorbate and vitamin C are completely dissolved in water, and water is used for quantification to make the total weight reach 100 grams to form a third premixed solution. Then, the quantified third premixed solution is filtered through an 80-mesh sieve to form a mixture. Herein, the mixtures of all groups contain 10 wt % of vitamin C respectively.

Next, each mixture is homogenized with a homogenizer (brand: GEA Niro Soavi, model: Panda Plus) at room temperature (25° C.) to form a liposome suspension, wherein the pressure value set in homogenization treatment is 350 bar. Moreover, the mixtures are subjected to a sterilization procedure, and the set value of the sterilization procedure is 95° C.±5° C. for 30 minutes. Herein, each liposome suspension contains a plurality of liposomes 1 in which vitamin C is encapsulated.

Example 3: Stability Experiment of a Standing Liposome Suspension

Herein, the liposome suspensions of all groups prepared in Example 1 and the liposome suspensions of all groups prepared in Example 2 are subjected to standing at room temperature (25° C.) for one day to observe whether or not the liposome suspensions are layered. In addition, if the liposome suspensions are uniform non-layered liquids, it means that the structure of the liposome 1 in the liposome suspensions is relatively stable. On the contrary, if the liposome suspensions are obviously layered with turbid and uneven colors, it means that the structure of the liposome 1 in the liposome suspensions is relatively unstable. In other words, because the encapsulating layer 10 of the liposome 1 is broken, the liposome 1 is not formed, and thus the liposome suspensions are obviously layered.

Figure 8:
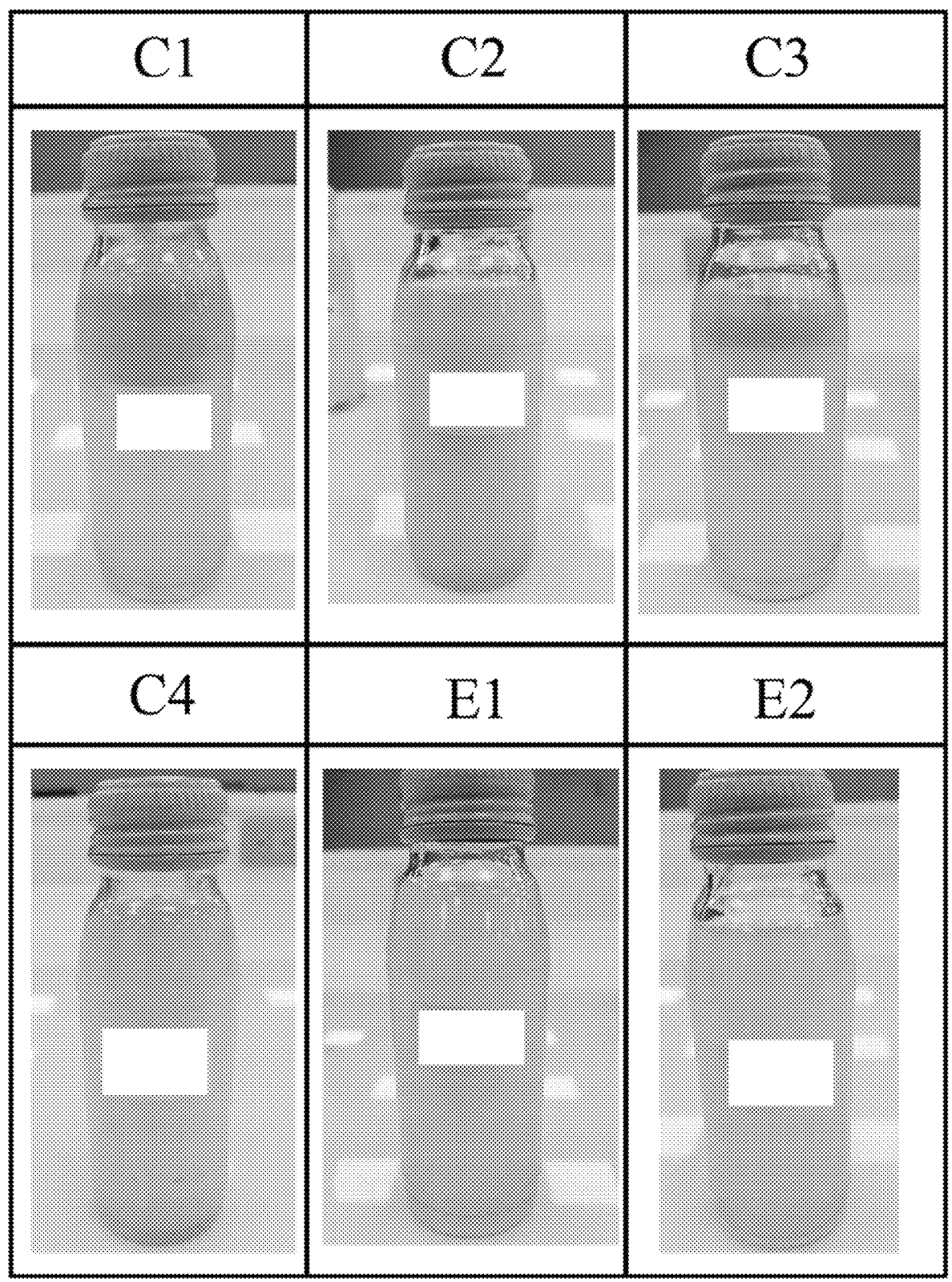
FIG. 8 is a stability experiment diagram of a standing liposome suspension in pre-sterilization treatment.

In reference to FIG. 8, the liposome suspensions of the groups C1 and C3 are obviously layered, indicating that when a mixture contains 1 wt % of soybean lecithin, 3 wt % or 5 wt % of Arabic gum cannot make soybean lecithin mixed with water uniformly, that is to say, an emulsification effect is not significant, and the structure of an obtained liposome 1 is unstable. Although the liposome suspensions of the groups C2 and C4 are not obviously layered, compared with the groups E1 and E2, the liposome suspensions of the groups C2 and C4 are more turbid. The liposome suspensions of the groups E1 and E2 are not obviously layered, indicating that when a mixture contains 0.1 wt % of soybean lecithin, 3 wt % or 5 wt % of Arabic gum can effectively make soybean lecithin mixed with water uniformly, and that is to say, an emulsification effect is significant. It can be seen that when a mixture contains 0.1 wt %-0.5 wt % of soybean lecithin and 3 wt %-5 wt % of Arabic gum, a liposome suspension obtained by pre-sterilization treatment of the mixture is not obviously layered. In other words, the liposome 1 prepared from 0.1 wt % of soybean lecithin and 3 wt %-5 wt % of Arabic gum has high structural stability.

Figure 9:
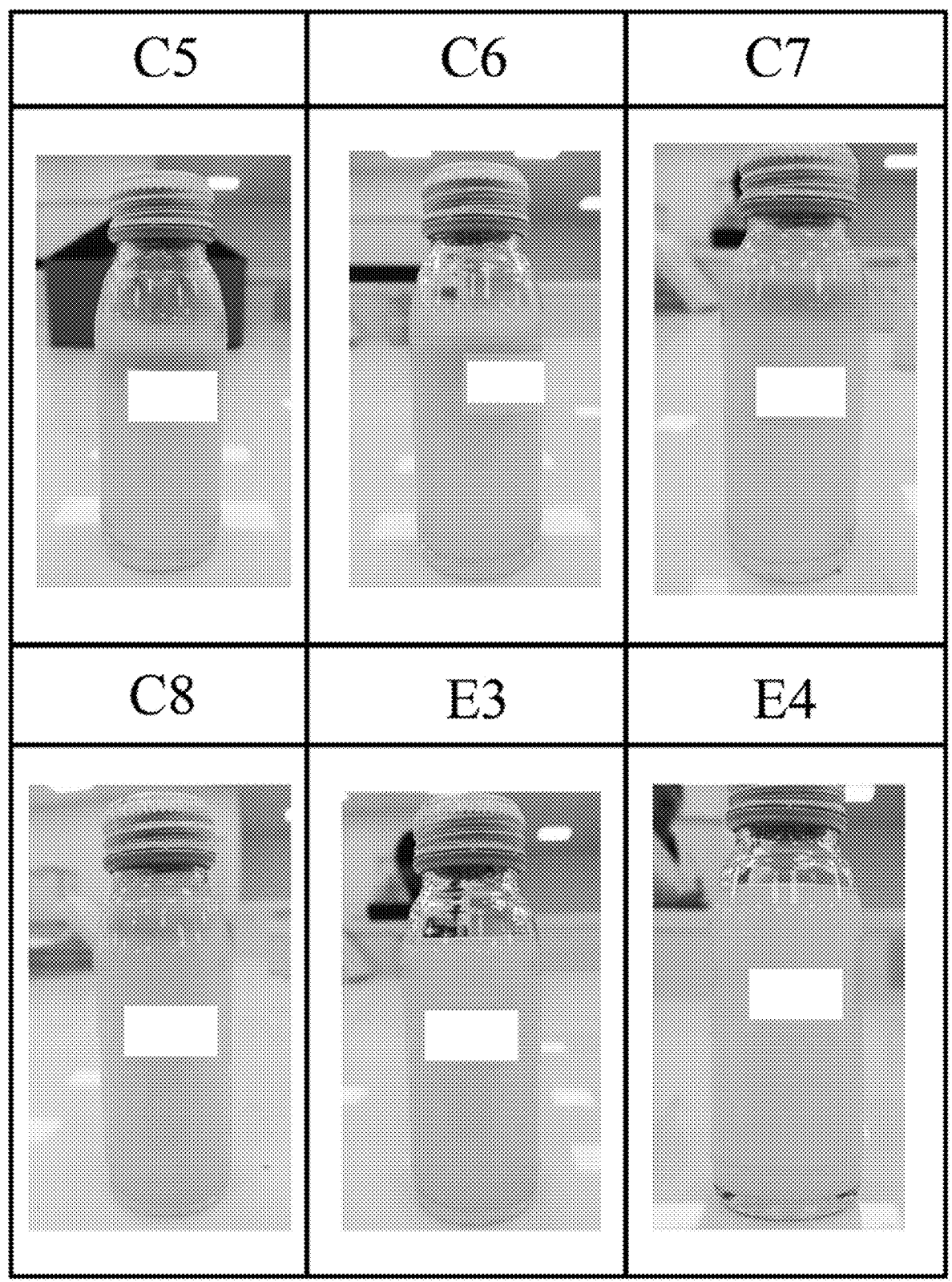
FIG. 9 is a stability experiment diagram of a standing liposome suspension in post-sterilization treatment.

In reference to FIG. 9, the liposome suspensions of the groups C5, C6, C7 and C8 are obviously layered, indicating that when a mixture contains 0.5 wt % or 1 wt % of soybean lecithin, 3 wt % or 5 wt % of Arabic gum cannot make soybean lecithin mixed with water uniformly, that is to say, an emulsification effect is not significant, and the structure of an obtained liposome 1 is unstable. Compared with the control groups, the liposome suspensions of the groups E3 and E4 are not obviously layered, indicating that when a mixture contains 0.1 wt % of soybean lecithin, 3 wt % or 5 wt % of Arabic gum can effectively make soybean lecithin mixed with water uniformly, and that is to say, an emulsification effect is significant. It can be seen that when a mixture contains 0.1 wt % of soybean lecithin and 3 wt %-5 wt % of Arabic gum, a liposome suspension obtained by post-sterilization treatment of the mixture is not obviously layered. In other words, the liposome 1 prepared from 0.1 wt % of soybean lecithin and 3 wt %-5 wt % of Arabic gum has high structural stability.

Example 4: Stability Experiment of a Centrifuged Liposome Suspension

Figure 10:
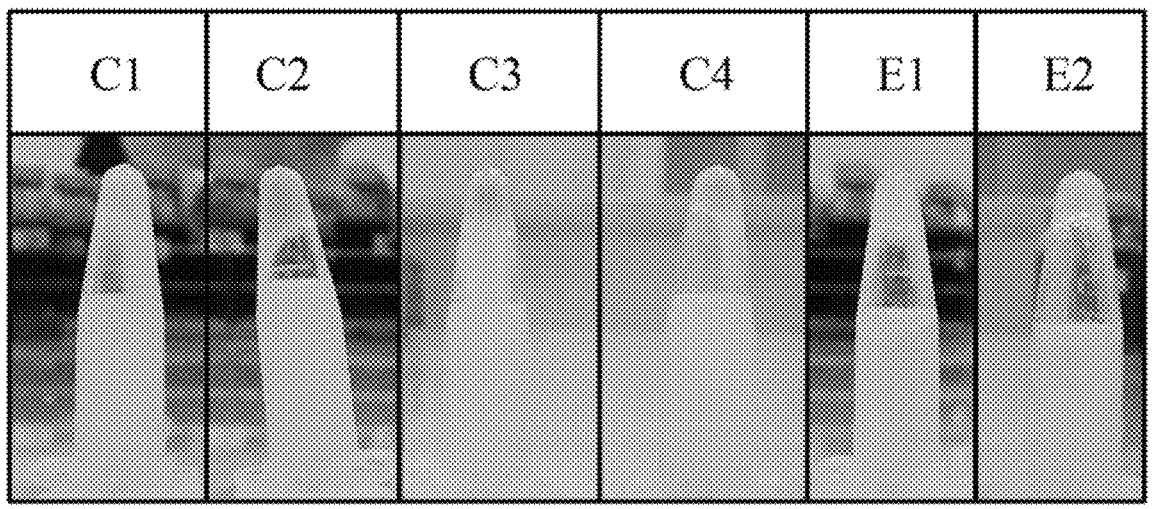
FIG. 10 is a stability experiment diagram of a centrifuged liposome suspension in pre-sterilization treatment.
Figure 11:
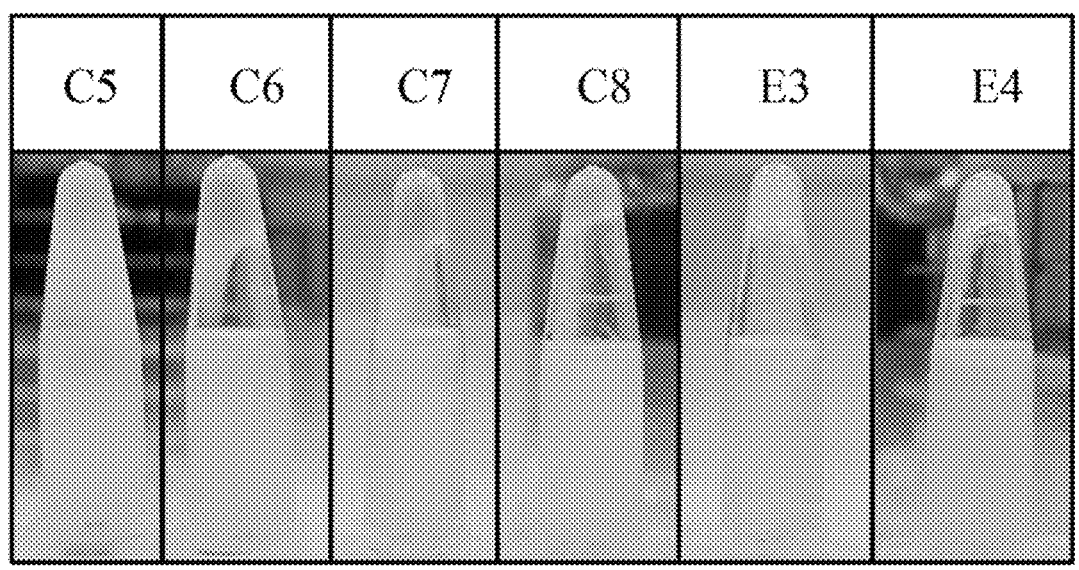
FIG. 11 is a stability experiment diagram of a centrifuged liposome suspension in post-sterilization treatment.

Herein, 1 ml of the liposome suspension of each group prepared in Example 1 and 1 mL of the liposome suspension of each group prepared in Example 2 are taken into a microcentrifuge tube separately. The liposome suspensions are centrifuged at 2000 rpm at 20° C.±5° C. for 1 hour to separate the liposome suspensions into supernatants and precipitates, as shown in FIG. 10 and FIG. 11. Herein, when the colors of the precipitates and the supernatants are obviously different, it means that the emulsification effects of the liposome suspensions are not significant, and the structures of the liposomes 1 contained in the liposome suspensions are relatively unstable.

In reference to FIG. 10, the liposome suspensions of the groups C1, C2, C3 and C4 have obvious precipitates after centrifugation, and the colors of the precipitates and the supernatants are obviously different, indicating that Arabic gum does not make soybean lecithin mixed water uniformly, and thus the obtained liposome suspensions are layered. Compared with the control groups, the precipitates of the groups E1 and E2 are not obvious, and the colors of the precipitates and the supernatants are less different, indicating that Arabic gum makes soybean lecithin mixed water uniformly, and thus the obtained liposome suspensions are not layered. It can be seen that the liposome 1 prepared from 0.1 wt % of soybean lecithin and 3 wt %-5 wt % of Arabic gum has high structural stability.

In reference to FIG. 11, the liposome suspensions of the groups C5, C6, C7 and C8 have obvious precipitates after centrifugation, and the colors of the precipitates and the supernatants are obviously different, indicating that Arabic gum does not make soybean lecithin mixed water uniformly, and thus the obtained liposome suspensions are layered. Compared with the control groups, the precipitates of the groups E3 and E4 are not obvious, and the colors of the precipitates and the supernatants are less different, indicating that Arabic gum makes soybean lecithin mixed water uniformly, and thus the obtained liposome suspensions are not layered. It can be seen that the liposome 1 prepared from 0.1 wt % of soybean lecithin and 3 wt %-5 wt % of Arabic gum has high structural stability.

It can be seen that no matter whether the sterilization procedure in the preparation process is pre-sterilization treatment or post-sterilization treatment, a liposome suspension prepared from 0.1 wt % of soybean lecithin and 3 wt %-5 wt % of Arabic gum has no oil slick phenomenon, and the plurality of liposomes 1 contained in the liposome suspension have high structural stability.

Example 5: Vitamin C Content Test

Herein, the supernatants and the precipitates obtained by centrifugation of the liposome suspensions of all groups in Example 4 are separately used as samples for detection of the content of vitamin C.

First, vitamin C (L-Ascorbic acid sodium; brand: SIGMA-ALORICH) standard products are prepared into 10 ppm, 25 ppm, 50 ppm, 100 ppm and 200 ppm standard solutions.

Then, 1 mL of the supernatants (samples) of all groups are added into a 100-mL quantitative bottles respectively, 0.1 gram of the precipitates (samples) of all groups are added into a 100-mL quantitative bottles respectively, and the samples are mixed with 100 mL of pure water and then subjected to ultrasonic oscillation (brand: DELTA, model: DC600H). Then, after ultrasonic oscillation, the samples are re-quantified to 100 mL with pure water to form test objects, and the test objects are filtered through a 0.22 μm filter membrane to form test solutions each of which contains a supernatant and a precipitate.

2 μL of each standard solution and 2 μL of detection solution of each group are taken separately and analyzed with an ultra-high performance liquid chromatographic instrument (brand: WATERS, model: H-class). A chromatography tube of the ultra-high performance liquid chromatographic instrument is a C18 column (Ascent's® Express C18 column, 2 μm, 2.1×100 mm (column number 17025-LC-037)), and a mobile phase used in the ultra-high performance liquid chromatographic instrument is a 0.1% oxalic acid aqueous solution (prepared with oxalic acid (purity≥98%); brand SIGMA-ALORICH). In addition, settings of the ultra-high performance liquid chromatographic instrument include: Flow rate 0.2 mL/minute, injection volume 2 μL, detection wavelength 245 nanometers (nm), column temperature 30° C., and injection frequency three times.

Then, the content of vitamin C in the test solutions can be obtained by comparing the wave peak retention time and absorption spectrum of the standard solutions and the test solutions, and the content of vitamin C in the supernatants (samples) and the precipitates (samples) can be obtained according to the following formula (1), as shown in Table 3.

Formula (1)

$$\text{The content of vitamin } C \text{ in a sample (ppm)} = C \times V \div M \quad (1)$$

wherein, C refers to the concentration (ppm) of vitamin C in a detection solution obtained according to a standard curve, V refers to the final constant volume (mL) of a sample, and M refers to the precipitate weight (g) or the supernatant volume (mL) of a sample for sampling analysis.

TABLE 3

| Treatment | Group | Supernatant (sample) (ppm) | Precipitate (sample) (ppm) |
| --- | --- | --- | --- |
| Pre-sterilization treatment | Group C1 | 3610 | 24460 |
| | Group C2 | 3570 | 24580 |
| | Group C3 | 3590 | 23590 |
| | Group C4 | 3330 | 23370 |
| | Group E1 | 3410 | 26390 |
| | Group E2 | 3440 | 32600 |
| Post-sterilization treatment | Group C5 | 3530 | 23620 |
| | Group C6 | 3440 | 21600 |
| | Group C7 | 3400 | 20620 |
| | Group C8 | 3310 | 29700 |
| | Group E3 | 3380 | 27540 |
| | Group E4 | 3420 | 36120 |

It can be seen from Table 3 that there is little difference in the measured content of vitamin C in the supernatants (test solutions or samples) of the pre-sterilization treatment groups (groups C1-C4 and groups E1-E2) or the post-sterilization treatment groups (groups C5-C8 and groups E3-E4). Then, the precipitates (test solutions or samples) of all pre-sterilization treatment groups and post-sterilization treatment groups are further compared. In the pre-sterilization treatment groups (groups C1-C4 and groups E1-E2), the measured content of vitamin C in the precipitates of the experimental groups (groups E1-E2) is higher than the measured content of vitamin C in the precipitates of the control groups (groups C1-C4). In the post-sterilization treatment groups (groups C5-C8 and groups E3-E4), the measured content of vitamin C in the precipitate of group E4 is much higher than the measured content of vitamin C in the precipitate of other groups, and the measured content of vitamin C in the precipitate of group E3 is higher than the measured content of vitamin C in the precipitate of groups C5-C7. It can be seen that under the same treatment conditions, the measured content of vitamin C in the precipitates of the experimental groups is obviously higher than the measured content of vitamin C in the precipitates of the control groups.

Herein, it can be seen that a liposome suspension prepared from 0.1 wt % of soybean lecithin and 3 wt %-5 wt % of Arabic gum contains a liposome 1 stably encapsulating vitamin C, and the liposome 1 has high structural stability. In addition, the contained liposome 1 can encapsulate many active ingredients (such as vitamin C).

Example 6: Electron Microscope

Herein, two groups of mixtures including an experimental group 1 and an experimental group 2 are prepared according to a formula in Table 4. The difference between the experimental group 1 and the experimental group 2 is that the mixture of the experimental group 1 contains 5 grams (5 wt %) of Arabic gum and 84.5125 grams of water, while the mixture of the experimental group 2 contains 2 grams of Arabic gum (2 wt %) and 87.5125 grams of water. The contents of other ingredients are the same. Then, according to the preparation steps described in Example 2, the prepared mixtures are subjected to steps such as homogenization treatment and sterilization procedure to form liposome suspensions.

TABLE 4

| | group | |
|---|---|---|
| Ingredient | Experimental group 1 | Experimental group 2 |
| Soybean lecithin | 0.1 | 0.1 |
| Arabic gum | 5 | 2 |
| Guar gum (thickener) | 0.0675 | 0.0675 |
| Sanxian gum (thickener) | 0.25 | 0.25 |
| Sucralose (sweetener) | 0.02 | 0.02 |
| Potassium sorbate (preservative) | 0.05 | 0.05 |
| Water | 84.5125 | 87.5125 |
| Vitamin C | 10 | 10 |

Unit: Grams (g), total weight 100 grams.

Figure 12:
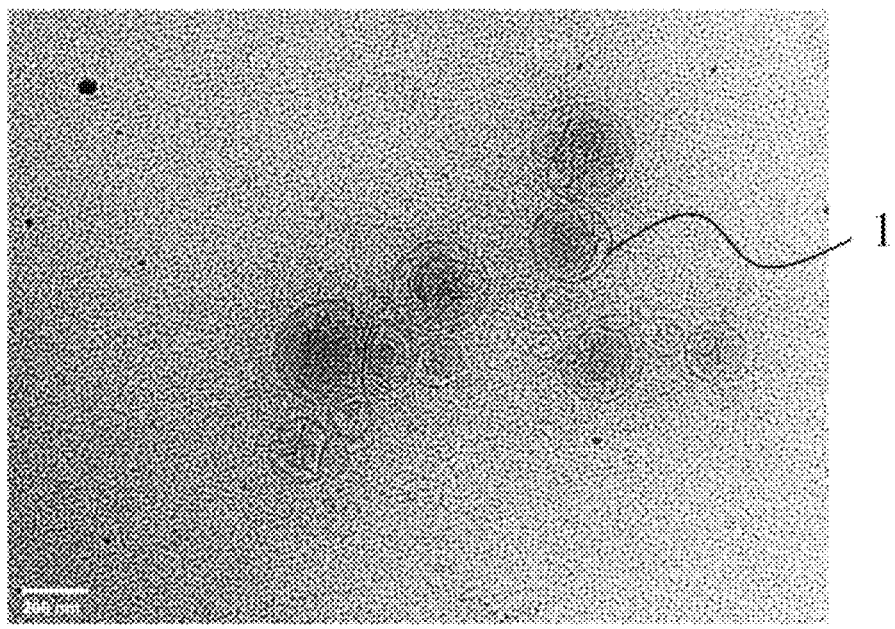
FIG. 12 is an electron micrograph of a liposome in an example.
Figure 13:
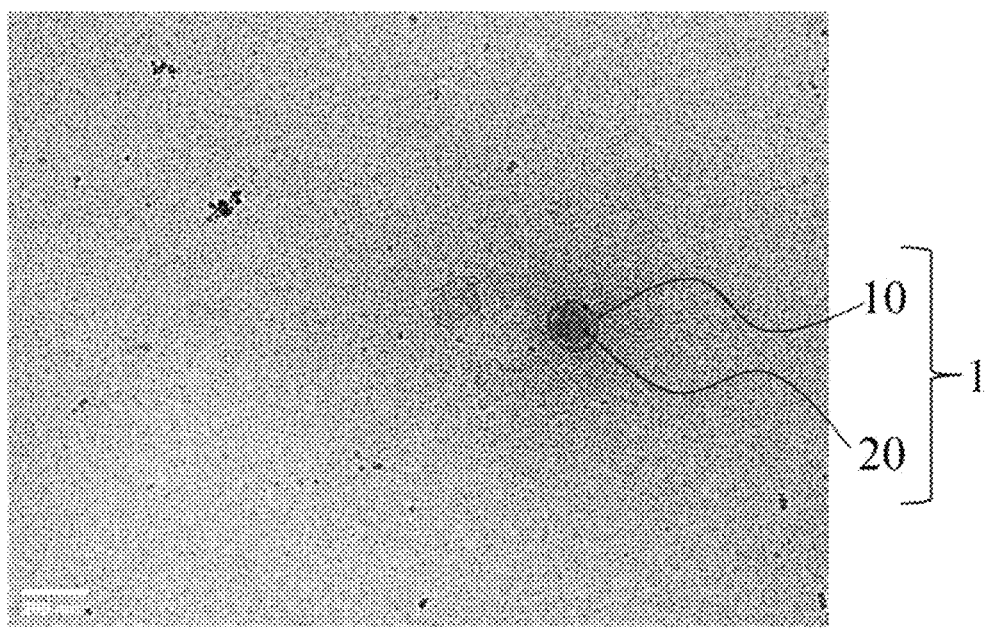
FIG. 13 is an electron micrograph of a liposome in another example.

Then, a cryo-electron transmission microscopy (cryo-TEM; brand: JEOL, model: JEM-1400) is used to observe the liposome 1 in the two groups of liposome suspensions, as shown in FIG. 12 and FIG. 13. In reference to FIG. 12, the liposome 1 is prepared from the mixture (containing 5 wt % of Arabic gum) obtained according to a formula of the experimental group 1, is spherical, and is about 200-400 nm long in outer diameter L. In addition, it can be seen from FIG. 12 that the same group of liposome suspension contains a plurality of liposomes 1 different in outer diameter L. In reference to FIG. 13, the liposome 1 is prepared by the mixture (containing 2 wt % of Arabic gum) obtained according to a formula of the experimental group 2 and is spherical, and an encapsulating layer 10 and an inner space 20 can be obviously observed. In other words, the liposome 1 is of a hollow spheric structure. In addition, the dark substance contained in the inner space 20 is vitamin C. It can be seen that the liposome suspensions prepared in the experimental group 1 and the experimental group 2 both contain the liposome 1 stably encapsulating vitamin C, and the structure of the liposome 1 is stable.

Herein, it can be seen that a liposome suspension prepared from 0.1 wt % of soybean lecithin and 2 wt %-5 wt % of Arabic gum contains a liposome 1 stably encapsulating vitamin C, and the liposome 1 is of a hollow spheric structure.

Example 7: Human Body Test

Herein, vitamin C supplements (hereinafter named test samples) of experimental groups and control groups are prepared according to a formula in Table 5. The test samples of the experimental groups are liposome-encapsulated vitamin C, and the test samples of the control groups are pure vitamin C solutions (rather than liposome-encapsulated vitamin C).

TABLE 5

| | group | |
|---|---|---|
| Ingredient | Experimental group | Control group |
| Lecithin | 10 | 0 |
| Arabic gum | 500 | 500 |
| Guar gum (thickener) | 6.75 | 6.75 |
| Corn sugar gum (Sanxian gum or xanthan gum) | 55 | 55 |
| Citric acid (acidifier) | 30 | 30 |
| Potassium sorbate (preservative) | 5 | 5 |
| Water | 8393.25 | 8403.25 |
| Vitamin C | 1000 | 1000 |

Unit: Milligrams (mg)

The preparation process of the experimental groups is as follows: 10 mg lecithin, 500 mg Arabic gum, 6.75 mg guar gum, 55 mg corn sugar gum, 30 mg citric acid, 5 mg potassium sorbate and 1000 mg vitamin C are dissolved in 8393.25 mg water and stirred uniformly to form a mixture. The mixture is homogenized at 350 bar at room temperature (25° C.) to form a liposome suspension, and then the liposome suspension is sterilized at 95° C.±5° C. for 30 minutes. Herein, the liposome suspension is prepared into a liquid package (10 ml/package) as a test sample of the experimental groups and taken by subjects.

The preparation process of the control groups is as follows: 500 mg Arabic gum, 6.75 mg guar gum, 55 mg corn sugar gum, 30 mg citric acid, 5 mg potassium sorbate and 1000 mg vitamin C are dissolved in 8403.25 mg water and stirred uniformly to form a mixture. Then the mixture is sterilized at 95°±5° C. for 30 minutes. On this basis, the sterilized mixture is prepared into a liquid package (10 mL/package) as a test sample of the control groups and taken by subjects.

Subject conditions: Healthy adults between 20 years-60 years of age.

Number of subjects: 10.

Experimental design: Subjects are subjected to a self-control cross-over experiment. The subjects take one test sample (liquid package of the experimental groups or the control groups) and then are subjected to primary detection, and the subjects take another test sample (liquid package of the control groups or the experimental groups) after 14 days and then are subjected to secondary detection. The day before each detection, the subjects need to fast for 8 hours; on the detection day, the time before the subjects take a test sample is regarded as 0 hour, and blood is collected at 0.5 hour, 1 hour, 2 hours, 3 hours, 4 hours and 8 hours to detect the concentration of vitamin C in the blood after the subjects take a test sample.

Detection method: At 6 time points of 0.5 hour, 1 hour, 2 hours, 3 hours, 4 hours and 8 hours after the subjects take a test sample, 4 ml of venous blood of each subject is collected as a sample by using a green-head blood collection tube containing an anticoagulant. The samples are subjected to standing in the dark at room temperature (25° C.) for 30 minutes. Then, the samples after standing are centrifuged at 3500 rpm at 4° C. for 10 minutes to collect sample supernatants (plasma), and the content of vitamin C in the collected plasma is measured by using biochemical colorimetry.

Figure 14:
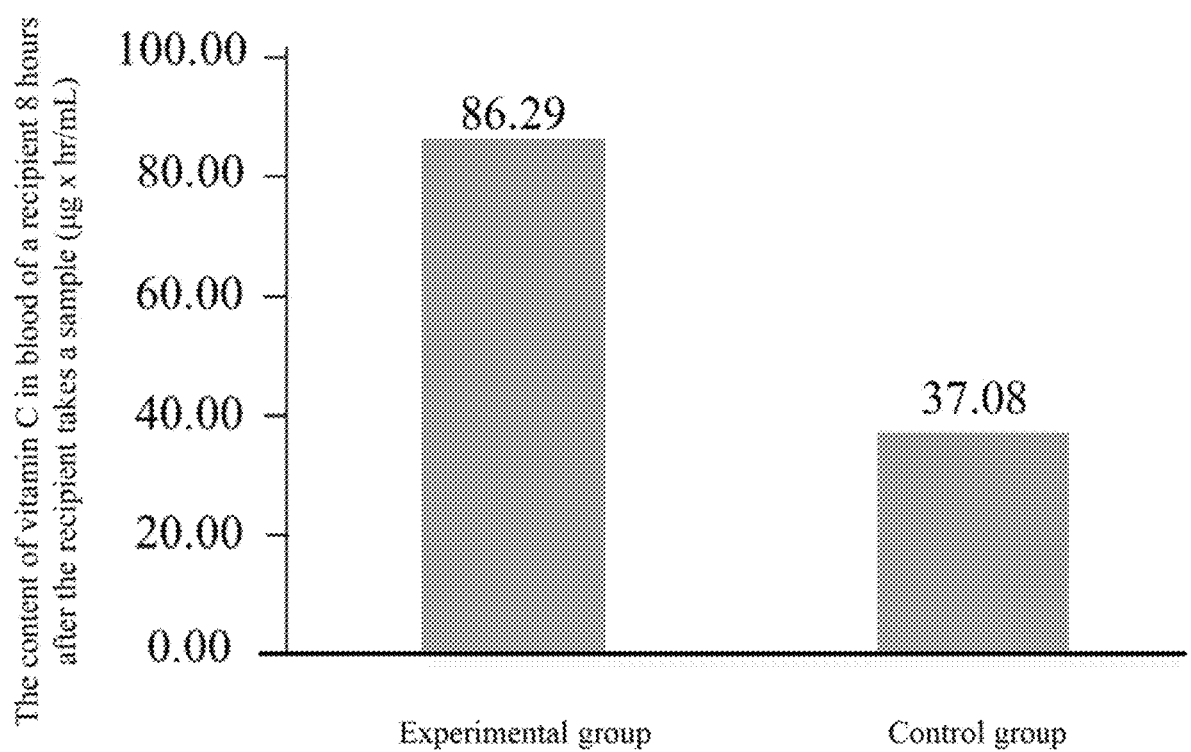
FIG. 14 is a data diagram showing the average content of vitamin C in the blood of recipients.

In reference to FIG. 14, 8 hours after the subjects take a test sample of the experimental groups, the measured content of vitamin C in the blood is 86.29 μg×hr/mL, and 8 hours after the subjects take a test sample of the control groups, the measured content of vitamin C in the blood is 37.08 μg×hr/mL. In other words, the content of vitamin C absorbed by the subjects in a test sample of the experimental groups is 133% higher than that of the control groups, indicating that the vitamin C supplements of liposome-encapsulated vitamin C can increase the bioabsorption rate.

It can be seen that when the liposome 1 is used to encapsulate an active ingredient and prepare a nutritional supplement of an active ingredient, the encapsulating layer 10 of the liposome 1 can protect the active ingredient located in the inner space 20, and the encapsulating layer 10 composed of bilayered phospholipids is conducive to increasing the bioabsorption rate of an active ingredient by a recipient.

In conclusion, a liposome 1 with a stable structure and good and stable encapsulating ability can be prepared by using a preparation method for a liposome 1 having the ability to stably encapsulate an active ingredient according to any example in the instant disclosure. In addition, the preparation method for a liposome having the ability to stably encapsulate an active ingredient according to any example can be used to prepare a liposome 1 which is stable in structure and can stably encapsulate an active ingredient. In this way, the content of an active ingredient encapsulated in a liposome 1 can be increased by a preparation method for a liposome having the ability to stably encapsulate an active ingredient according to any example, and the prepared liposome 1 can increase the bioabsorption rate of the active ingredient by a recipient.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A preparation method for a liposome having an ability to stably encapsulate an active ingredient, comprising:
   providing a mixture, wherein the mixture comprises 0.1 wt % of lecithin, 2 wt %-5 wt % of Arabic gum, the active ingredient, and 63.9125 wt %-97.9 wt % of a solvent; and
   homogenizing the mixture at 300 bar-400 bar to form a liposome suspension, wherein the liposome suspension comprises a plurality of liposomes,
   wherein the solvent is water, and the active ingredient is vitamin C.

2. The preparation method according to claim 1, wherein the active ingredient is present in the mixture at 5-30 wt %.

3. The preparation method according to claim 2, wherein the active ingredient is present in the mixture at 10 wt %.

4. The preparation method according to claim 1, wherein the step of providing the mixture comprises:
   stirring 0.1 wt % of lecithin, 2 wt %-5 wt % of Arabic gum, the active ingredient, and 63.9125-97.9 wt % of the solvent to form a premixed solution; and
   filtering the premixed solution through an 80-mesh sieve to form the mixture.

5. The preparation method according to claim 1, wherein the mixture is homogenized at 40° C.-60° C., and the method further comprises:
   sterilizing the mixture at 95° C. for 30 minutes before homogenization.

6. The preparation method according to claim 1, wherein the mixture is homogenized at room temperature, and the method further comprises:
   sterilizing the liposome suspension at 95° C. for 30 minutes after homogenization.

7. The preparation method according to claim 1, wherein each liposome has a hollow spheric structure.

* * * * *